US005567427A

United States Patent [19]
Papadakis

[11] Patent Number: 5,567,427
[45] Date of Patent: Oct. 22, 1996

[54] EMULSIFIED, LOW PH COSMETIC COMPOSITIONS HAVING IMPROVED STABILITY

[75] Inventor: Marcelline C. Papadakis, Berwyn, Ill.

[73] Assignee: Helene Curtis, Inc., Chicago, Ill.

[21] Appl. No.: 406,106

[22] Filed: Mar. 17, 1995

[51] Int. Cl.$^6$ ........................................ A61K 7/42
[52] U.S. Cl. .......................... 424/401; 514/937; 514/938; 514/939; 514/943
[58] Field of Search ........................... 424/401; 514/937, 514/938, 939, 943

[56] References Cited

U.S. PATENT DOCUMENTS

| | | | |
|---|---|---|---|
| 4,209,499 | 6/1980 | Mayhew et al. | 260/403 |
| 4,503,002 | 3/1985 | Mayhew et al. | 260/945 |
| 5,073,372 | 12/1991 | Turner et al. | 424/401 |

OTHER PUBLICATIONS

M. Takahashi et al., "The influence of hydroxy acids on the rheological properties of statum corneum," *J. Soc. Cosmet. Chem.*, 36 (Mar./Apr. 1985), pp. 177–187.

D. L. Fost, "Cationic Emulsification In Creams & Lotions," *Drug and Cosmetic Industry*, Oct. 1985 (reprint).

M. Asnes, "A Skin Miracle," *Mirabella*, Jan. 1993, pp. 60–61.

Anon, "Fruit Acids: The New Beauty Miracle," pp. 76–77.

R. Berg, "Fruit Juice," *New York Times*, Dec. 12, 1992, p. 74.

*Primary Examiner*—Jyothsna Venkat
*Attorney, Agent, or Firm*—Marshall, O'Toole, Gerstein, Murray & Borun

[57] ABSTRACT

Emulsified, low pH cosmetic compositions having improved pH stability and phase stability are disclosed. The emulsified cosmetic compositions have a pH of about 3.7 to about 4.5, and contain about 10% to about 50% by weight of a dispersed oil phase, about 2% to about 20% by weight of an acid, like a hydroxycarboxylic acid, and about 0.5% to about 2% of a quaternized phosphate ester, like linoleamidopropyl PG-dimonium chloride phosphate. The emulsified cosmetic compositions are phase stable over an extended storage period and maintain an essentially constant pH by exhibiting a pH drift of about 0.15, and usually 0.1, pH unit or less.

11 Claims, No Drawings

EMULSIFIED, LOW PH COSMETIC COMPOSITIONS HAVING IMPROVED STABILITY

FIELD OF THE INVENTION

The present invention relates to emulsified, low pH cosmetic compositions having improved pH stability and improved phase stability. In particular, the present invention relates to emulsified cosmetic compositions containing an acid, like a hydroxycarboxylic acid, and to improving the storage stability and reducing the pH drift of the emulsified cosmetic compositions by incorporating about 0.5% to about 2%, by weight, of a quaternized phosphate ester into the cosmetic composition.

BACKGROUND OF THE INVENTION

Emulsified, low pH cosmetic compositions have been sold to consumers for the purpose of providing smoother, younger-looking skin. The emulsified cosmetic compositions often contain an organic acid, such as a hydroxycarboxylic acid, hereafter termed a "hydroxy acid", and typically contain an α-hydroxycarboxylic acid, hereafter termed an "α-hydroxy acid". Other types of organic acids are included in cosmetic compositions as emollients.

Emulsified cosmetic compositions containing a hydroxy acid act to smooth fine lines in the skin and lighten skin dark spots caused by photoaging, i.e., skin damage resulting from excessive exposure to the sun. The emulsified, low pH cosmetic compositions originally were available only by prescription, but over the last several years several over-the-counter compositions have become available to consumers. The over-the-counter compositions generally include low weight percentages of a hydroxy acid, e.g., up to about 8% by weight. The over-the-counter hydroxy acid compositions make skin smoother and help skin retain moisture better.

The acid present in cosmetic compositions often is a hydroxycarboxylic acid, generally an α-hydroxycarboxylic acid, like glycolic acid. However, some low pH cosmetic compositions incorporate acids other than hydroxy acids. The α-hydroxy acids have been used by dermatologists for over twenty-five years to treat eczema, psoriasis and ichthyosis, an inherited skin condition. α-Hydroxy acids also effectively treat dry, flaking skin on the hands caused by excessive exposure to detergents.

On normal skin, a hydroxy acid works as an exfoliant to facilitate shedding of dead skin cells from the skin surface and facilitate replacement of the dead cells with new skin cells at a faster rate. Exfoliation is a normal skin regeneration process, but aging and exposure to the sun slows exfoliation. Individuals therefore lose the ability to efficiently shed dead skin cells, and as a result the skin gets flaky. The cells therefore shed in clumps, and the skin is perceived as dry. A hydroxy acid stimulates skin cells to shed faster and more smoothly. A hydroxy acid therefore normalizes the scaling process and weakens the bonds between scales in photoaged skin. By normalizing the skin's outer layer, a hydroxy acid also improves the skin to ability to hold moisture.

In particular, dermatologists apply compositions having a high concentration of hydroxy acid (50 to 70 weight percent) for superficial peels, to smooth rough skin, and to remove fine lines, acne scars, age spots, irregular pigmentation, and precancerous scaly patches. Dermatologists and salon professionals use compositions having a moderate hydroxy acid concentration (10 to 50 percent) to help control acne by unplugging pores, and to enhance the effectiveness of Retin-A and skin bleaches. At these concentrations, the hydroxy acid-containing products often provide dramatic results, but the potential to irritate or burn the skin is high. At hydroxy acid concentrations of 30% by weight or more, the compositions are capable of chemically burning the skin.

A low pH cosmetic composition generally is applied after cleansing and toning the skin, and before moisturizing. Some acid-containing compositions also contain a moisturizer, which eliminates the final moisturizing step. With regular use, the hydroxy acid-containing compositions essentially eliminate the need to use a mechanical exfoliator, such as a scrub.

Compositions containing a hydroxy acid or other organic acid are acidic in nature and have a low pH. Accordingly, there is a need to balance the acidic nature of an emulsified, low pH cosmetic composition with the irritation potential of the composition because acid-containing compositions have a strong skin irritation potential. Many acid-containing compositions, including hydroxy acid-containing compositions, warn the user that a tingling or burning sensation may be felt after the first several applications of the composition to the skin. For esthetics and consumer confidence it is important to minimize the tingling or burning sensation. In addition, for prescription compositions and compositions used in doctor's offices, it is advantageous to reduce the possibility of a chemical burn, or the irritation caused by a more aggressive acid treatment, such as a skin peel or an acne scar removal.

One problem encountered in formulating emulsified, low pH cosmetic products containing an acid is pH drift. During storage, an emulsified, low pH composition typically exhibits a downward pH drift of at least about 0.2, and usually about 0.3, pH units. This downward drift in pH increases the acidity of the composition, and accordingly increases the skin irritation potential of composition. The pH drift also can lead to emulsion instability thereby causing phase separation during storage.

Phase separation is an important problem to overcome because the cosmetic compositions typically are emulsified creams or lotions. Phase separation can lead to an acid concentration in the water phase which either reduces product efficacy if the predominantly oil phase is applied to the skin, or increases skin irritation potential if the predominantly water phase is applied to the skin. The present invention is directed to overcoming these problems and providing pH-stabilized and phase-stabilized, emulsified cosmetic compositions containing an acid, and particularly a hydroxy acid.

SUMMARY OF THE INVENTION

The present invention is directed to emulsified, low pH cosmetic compositions having improved storage stability and improved pH stability. In particular, the emulsified, low pH cosmetic compositions have a pH of about 3.7 to about 4.5, and comprise about 2% to about 20% by weight of an acid, typically a hydroxy acid; about 10% to about 50% by weight of an oil phase; and about 0.5% to about 2.0% of a quaternized phosphate ester.

In accordance with one important aspect of the present invention, the emulsified, low pH cosmetic compositions have a pH drift of about 0.15 pH unit or less, and usually about 0.1 pH unit or less, thereby maintaining composition mildness and emulsion stability.

Another important aspect of the present invention is to provide a method of improving the stability of an emulsified, low pH cosmetic composition by incorporating a sufficient amount of a quaternized phosphate ester into the composition such that the composition has a pH shift of about 0.15 pH unit or less, and preferably about 0.1 pH unit or less.

Yet another aspect of the present invention is to provide an emulsified, low pH cosmetic composition that is phase stable over the expected life of the composition.

Another important aspect of the present invention is to provide an emulsified, low pH cosmetic composition comprising an acid capable of treating the skin, wherein the composition maintains an essentially constant pH over the lifetime of the composition. The acid can be a carboxylic acid, like orotic acid or urocanic acid, but other organic acids, like uric acid, also can be used in the emulsified cosmetic composition.

Another important aspect of the present invention is to provide an emulsified, low pH cosmetic composition comprising an organic acid, like an α-hydroxycarboxylic acid (e.g., glycolic acid), a β-hydroxycarboxylic acid (e.g., β-hydroxypriopionic acid), or a combination thereof, that maintains an essentially constant pH over the lifetime of the composition. The hydroxy acid can be an aliphatic acid (e.g., lactic acid), or an aromatic acid (e.g., salicylic acid or mandelic acid).

Yet another aspect of the present invention is to incorporate about 0.5% to about 2% by weight of a quaternized phosphate ester having general structural formula I into an emulsified, low pH cosmetic composition. The quaternized phosphate ester maintains the emulsified composition at an essentially constant pH, i.e., the composition exhibits a pH drift of about 0.15, and preferably about 0.1, pH unit or less. Quaternized phosphate ester I has the structure:

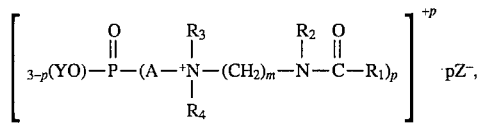

wherein $R_1$ is an aryl, an alkaryl, an alkyl, or an alkenyl group, or a hydroxyalkyl group, wherein the alkyl or hydroxyalkyl group includes about seven to about 21 carbon atoms; $R_2$ is hydrogen or an alkyl or a hydroxyalkyl group including one to about six carbon atoms; $R_3$ and $R_4$, independently, are an alkyl or a hydroxyalkyl group including one to about six carbon atoms; A is a residue of a glycol or a triol having two to about four carbon atoms, such as the residue of propylene glycol ($-OCH_2CH(OH)CH_2-$); Z is an anion; m is a numeral from one to about 10; Y is selected from the group consisting of hydrogen, an alkyl group, a hydroxyalkyl group, and an aryl group, either substituted or unsubstituted, and wherein the alkyl or the hydroxyalkyl group includes one to about 22 carbon atoms; and p is a number from 1 to 3.

The above and other aspects and advantages of the present invention will become apparent from the following detailed description of the preferred embodiments.

DETAILED DESCRIPTION OF THE PREFERRED EMBODIMENTS

The present composition is an emulsified, low pH cosmetic composition that exhibits improved pH stability and improved phase stability. The emulsified composition comprises a continuous aqueous phase and a dispersed oil phase. The oil phase is present in an amount of about 10% to about 50% by weight of the emulsified composition. The aqueous phase comprises about 2% to about 20% by weight of an acid, typically a hydroxycarboxylic acid, and about 0.5% to about 2% by weight of a quaternized phosphate ester. The emulsified cosmetic composition has a pH of about 3.7 to about 4.5, and exhibits a pH drift of about 0.15, and preferably about 0.1, pH unit or less, i.e., maintains an essentially constant pH.

The present emulsified cosmetic composition is designed for topical application to the skin. The compositions are lotions or creams. The acid present in the composition either acts as an exfoliant to assist removal of dead skin cells and to smooth the skin, e.g., a hydroxy acid, and/or acts as a skin conditioning agent, e.g., orotic acid. The oil phase incorporates emollients and compounds that enhance the lubricity and feel of the composition. The quaternized phosphate ester improves the pH and phase stability of the composition. Emulsifiers are included to provide a stable, thick emulsion. Thickeners also can be included in the composition to help stabilize emulsified compositions having an oil phase of about 10% to about 20% by weight.

In accordance with an important feature of the present invention, an emulsified, low pH composition includes about 2% to about 20% of an acid, and typically a hydroxy acid. The emulsified composition preferably contains about 3% to about 15% by weight of an acid. To achieve the full advantage of the present invention, the emulsified cosmetic composition contains about 3% to about 12% by weight of an acid.

The acid conventionally incorporated into the emulsified composition is a hydroxy acid. Hydroxy acids act as exfoliants to help remove dead skin cells from the skin. The particular amount of hydroxy acid included in the composition is dependent upon the identity of the applicator, i.e., a consumer, a skin care professional, or a doctor, and the intended end use for the composition, i.e., a cosmetic or a dermatological drug. However, below about 2% by weight, an insufficient amount of hydroxy acid is present in the composition to observe smoother skin within a reasonable time period. The composition containing less than about 2% by weight hydroxy acid is efficacious, but works at such a slow rate that the benefits of a hydroxy acid are not observed by the consumer within an acceptable timeframe. Above about 20% by weight, the hydroxy acid is present in such a high amount that the advantages of reduced pH drift are swamped. For example, it is theorized that the benefit of reducing skin irritation by abating composition pH drift from about 0.2–0.3 pH units to about 0.15 pH unit or less is not observed because the high percentage of hydroxy acid in the composition (i.e., above about 20% by weight) is inherently irritating to the skin.

The hydroxy acid, or any other organic acid, in the emulsified composition can be present in the free acid form, in the salt form, or as a mixture of the free acid and salt form. Often, the acid is present as a mixture of the free acid form and salt form in order to provide a composition having a pH of about 3.7 to about 4.5, and preferably a pH of about 3.8 to about 4.3. To achieve the full advantage of the present invention, the emulsified composition has a pH of about 3.8 to about 4.1. Below a pH of about 3.7, the emulsified composition has a tendency to irritate the skin of a substantial number of consumers, and therefore would not be a commercially acceptable composition. Above a pH of about 4.5, it has been theorized that a hydroxy acid is neutralized in a sufficient amount such that the ability of the composition to act as an exfoliant is decreased.

When the hydroxy acid is present in the salt form, the hydroxy acid is neutralized with a water-soluble alkali until the desired pH is achieved. The water-soluble alkali can be for example, ammonia or ammonia hydroxide, a water-soluble amine, or an alkali metal hydroxide. Preferred water-soluble alkalis include but are not limited to ammonia, ammonium hydroxide, diethanolamine, triethylamine, methylamine, triethanolamine, potassium hydroxide, sodium hydroxide, lithium hydroxide, or a primary, secondary or tertiary amine having alkyl or hydroxyalky groups containing one to three carbon atoms.

A hydroxy acid present in the emulsified cosmetic composition is an organic acid containing at least one hydroxyl group (i.e., an OH group) and at least one carboxylic acid group (i.e., a $CO_2H$ group). An α-hydroxycarboxylic acid is the preferred hydroxy acid, although β-hydroxycarboxylic acids (i.e., β-hydroxy acids) also are useful exfoliants and can be used in the emulsified composition.

The identity of the hydroxy acid present in the emulsified composition is not limited as long as the hydroxy acid acts as an exfoliant and is capable of smoothing the skin. The hydroxy acid can be an aliphatic acid, e.g., glycolic acid; an aromatic acid, e.g., salicylic acid; or have aromatic and aliphatic components, e.g., mandelic acid.

Exemplary hydroxy acids include the α-hydroxy acids, such as, but not limited to, glycolic acid, citric acid, lactic acid, tartaric acid and malic acid. These α-hydroxy acids are naturally-occurring acids found in fruit, and have been used in skin care and skin treatment compositions for several years. It has been theorized that glycolic acid and lactic acid are the most effective α-hydroxy acids because these acid molecules are small and more able to penetrate skin. Hydroxycaprylic acid is a synthetic α-hydroxy acid that has been used in skin care compositions. Other useful α-hydroxy acids are, for example, mandelic acid, leucic acid and ethylglycolic acid.

β-hydroxy acids, like salicylic acid, β-hydroxypropionic acid and β-hydroxybutyric acid, also are useful in the emulsified composition of the present invention. In general, any aliphatic α- or β-hydroxy acid having an aliphatic carbon chain containing two through ten carbon atoms is useful in the emulsified cosmetic composition. The hydroxy acid can be a monocarboxylic acid, a dicarboxylic acid or a polycarboxylic acid.

The acid in the emulsified, low pH cosmetic composition is not limited to hydroxy acids, Essentially any acid that is used in cosmetic compositions to treat the skin can be incorporated into the present composition and the benefit of an essentially constant pH is observed. The acids traditionally are organic acids.

Specific acids that can be incorporated into the emulsified cosmetic composition include, but are not limited to, glucuronic acid, glutamic acid, allantoin galacturonic acid, allantoin glycyrrhetinic acid, allantoin polygalacturonic acid, animal collagen amino acids, animal elastin amino acids, animal keratin amino acids, aspartic acid, folic acid, hyaluronic acid, linoleic acid, linolenic acid, orotic acid, palmitoyl animal collagen amino acids, ribonucleic acid, silk amino acids, uric acid, urocanic acid, dilinoleic acid, trilinoleic acid, alanine, 6-aminocaproic acid, arginine, asparagine, carbocysteine, cysteine, cystine, glycine, histidine, hydroxyproline, isoleucine, leucine, lysine, methionine, phenylalanine, proline, serine, threonine, tryptophan, tyrosine, biotin, o-cresotic acid, glycyrrhetinic acid, glycyrihizic acid, lanolin acid, and mixtures thereof. Other organic acids, either carboxylic acids, amino acids, or an organic acid having an ionizable hydrogenated atom, also can be incorporated into the present emulsified cosmetic composition.

In addition to the acid, which is present in the continuous aqueous phase of the emulsified cosmetic composition, the emulsified composition includes a dispersed oil phase. The oil phase is present in an amount of about 10% to about 50% by weight of the composition, and preferably about 15% to about 40%, by weight of the composition. To achieve the full advantage of the present invention, the oil phase is present in an amount of about 17% to about 30%, by weight of the composition.

If the oil phase is present in an amount less than about 10% by weight of the composition, then an insufficient amount of oil phase is present to provide the desired esthetic effects, e.g., lubricity, skin feel or emolliency. When the organic phase is present above about 50% by weight of the composition, the composition becomes too costly to be commercially practicable and the composition begins to lose desired esthetic properties, i.e., the composition becomes too oily or has a greasy feeling.

In addition, if the oil phase is present in an amount of about 10% to about 20% by weight of the composition, then the viscosity of the composition is sufficiently low such that the oil phase separates from the aqueous phase. Therefore, an organic polymer or an organic or inorganic thickener is incorporated into the emulsified composition to help disperse the oil phase in the continuous aqueous phase.

Exemplary polymers and thickeners are listed in the *CTFA Cosmetic Ingredient Handbook*, 1st Ed., J. M. Nikitakis ed., The Cosmetic, Toiletry and Fragrance Association, Washington, DC (1988) (hereafter *CTFA Handbook*), at pages 30, 47, 48, 67 and 97–100, incorporated herein by reference. Preferred thickening agents are magnesium aluminum silicate, sold under the tradename VEEGUM and available in various grades from R. T. Vanderbilt Co., Inc., Norwalk, Conn.; aluminum starch octenylsuccinate; a water-soluble polymer, like a polyvinylalcohol, a polybutene, a polyethylene glycol, or a polyethylenimine; or a gum, like xanthan gum, hydroxyethylcellulose, karaya gum, carrageenen, hydroxypropyl guar, methylcellulose, tragacanth gum, or hydroxypropylcellulose.

Compounds included in the oil phase typically are lubricating agents, bodifiers, viscosity enhancers, emollients, or compounds that improve the feel of the composition on the skin. Exemplary types of compounds present in the dispersed oil phase include, but are not limited to, a silicone, a hydrocarbon, an oil, a fat, a wax, a water-insoluble fatty alcohol or fatty acid having about 8 to about 22 carbon atoms, or a water-insoluble fatty ester having about 9 to about 34 carbon atoms.

In particular, the silicone can be a polyalkyl siloxane, a polyaryl siloxane, a polyalkylaryl siloxane, or a mixture thereof. The silicone can be a nonvolatile silicone, like a polydimethylsiloxane fluid or a polydimethylsiloxane gum. Preferred silicone fluids and gums include linear and branched polydimethylsiloxanes of the following general formula:

$(CH_3)_3SiO—[Si(CH_3)_2O]_n—Si(CH_3)_3$, wherein n is a number from 2,000 to about 15,000, and preferably from about 2,000 to about 7,000. Silicone fluids and gums useful in emulsified compositions of the present invention are available from numerous commercial sources, including General Electric Company, Waterford, N.Y., and Dow Corning Corp., Midland, Mich. The nonvolatile polydimethylsiloxane compounds typically are nonfunctional siloxanes having a viscosity of about 5 to about 600,000 cs (centistoke), and preferably about 350 to about 10,000 cs, at 25° C.

A volatile silicone also can be used in the oil phase, either alone or in conjunction with other water-insoluble compounds. The volatile silicone normally is a low molecular weight polydimethylsiloxane, however a low molecular weight polydimethylsiloxane including phenyl substituents also is useful in the compositions of the present invention. Furthermore, the low molecular weight polydimethylsiloxane compound can be a linear or a cyclic polydimethylsiloxane compound.

An example of a linear, low molecular weight, volatile polydimethylsiloxane compound useful in a composition of the present invention is hexamethyldisiloxane, available commercially under the tradename DOW CORNING 200 FLUID, from Dow Corning Corp., Midland, Mich. Hexamethyldisiloxane has a viscosity of 0.65 cs (centistokes). Other linear polydimethylsiloxanes, such as decamethyltetrasiloxane, having a boiling point of about 195° C. and a viscosity of 1.5 centistokes; octamethyltrisiloxane; and dodecamethylpentasiloxane, also are useful in the composition of the present invention.

In addition, the cyclic, low molecular weight, volatile polydimethylsiloxanes, having the Cosmetic, Toiletry and Fragrance Associate (CTFA) designation cyclomethicones, also are useful in the composition and method of the present invention. The cyclomethicones are low molecular weight, water-insoluble cyclic compounds having an average of about 3 to about 6 —[O—Si(CH$_3$)$_2$]— repeating group units per molecule and boil at atmospheric pressure in a range of about 150° C. to about 250° C. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, N.Y., and SILICONE 334 FLUID and SILICONE 345 FLUID from Dow Corning Corporation, Midland, Mich., the tetramer being listed first in each instance. The volatile cyclic silicones can be used in combination with a linear volatile silicone, and the volatile silicones can be used in conjunction with the nonvolatile silicones.

Another suitable compound that can be included in the oil phase of the present emulsified composition is a nonvolatile hydrocarbon, such as mineral oil. The nonvolatile hydrocarbons provide many of the same benefits as the silicone compounds, and can be included in the emulsified composition in conjunction with a silicone.

A volatile hydrocarbon compound can be included in the oil phase of the composition, either alone or in conjunction with other water-insoluble compounds. A volatile hydrocarbon has about 10 to about 26 carbon atoms. A preferred volatile hydrocarbon compound is an aliphatic hydrocarbon having about 12 to about 24 carbon atoms, and a boiling point in the range of about 100° C. to about 300° C. Exemplary volatile hydrocarbons are depicted in general structural formula II, wherein n ranges from 2 to 5.

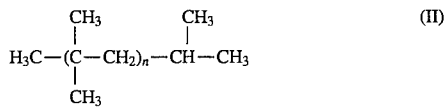

Examples of volatile hydrocarbons useful in the emulsified compositions of the present invention are the commercially-available compounds PERMETHYL 99A and PERMETHYL 101A, corresponding to compounds of general structural formula II wherein n is 2 and 3, respectively, from Permethyl Corporation, Frazer, Pa. A volatile hydrocarbon compound is useful in the emulsified composition of the present invention either alone, in combination with another volatile or nonvolatile hydrocarbon, or in combination with a volatile or nonvolatile silicone.

The oil phase also can include a fatty ester having about 9 to about 34 carbon atoms. The fatty component of the fatty ester can be derived from a fatty acid or a fatty alcohol, or a combination thereof. In addition, the fatty ester can be a straight chain fatty ester, like isopropyl myristate; a branched chain fatty ester, like Purcellin Oil; a benzoate ester, like C$_{12-15}$ alcohols benzoate; or a combination thereof.

For example, a useful class of fatty esters is derived from carboxylic acids having about 6 to about 12 carbon atoms, including both branched and straight chain carboxylic acids. In general, the C$_6$ to C$_{12}$ carboxylic acid is esterified with a fatty alcohol including about 12 to about 22 carbon atoms to provide a fatty (C$_{12}$ to C$_{22}$) ester of a C$_6$ to C$_{12}$ carboxylic acid that is useful in the present invention. Such fatty alcohols include, but are not limited to, lauryl alcohol, myristyl alcohol, cetyl alcohol, cetearyl alcohol, stearyl alcohol, isostearyl alcohol, oleyl alcohol, tallow alcohol, behenyl alcohol and mixtures thereof. Accordingly, fatty (C$_{12}$ to C$_{22}$) esters of C$_6$ to C$_{12}$ carboxylic acids useful in the composition and method of the present invention include, but are not limited to, cetyl octanoate, stearyl heptanoate, stearyl caprylate, stearyl octanoate, lauryl octanoate, myristyl heptanoate, and oleyl octanoate, or mixtures thereof. These fatty esters can occur naturally or can be synthesized.

In place of, or in combination with, the fatty (C$_{12}$ to C$_{22}$) ester of a C$_6$ to C$_{12}$ carboxylic acid, a fatty ester derived from a fatty acid including about 8 to about 22 carbon atoms esterified with an alcohol including 1 to about 6 carbon atoms can be included in the composition of the present invention. Examples of such fatty esters include, but are not limited to, isopropyl myristate, isopropyl palmitate, isopropyl laurate, isopropyl linoleate, isopropyl tallowate, isopropyl ricinoleate, methyl laurate, methyl linoleate, methyl myristate, methyl stearate, methyl ricinoleate, methyl caprylate, methyl oleate, methyl palmitate, methyl stearate, methyl behenate, methyl soyate, methyl tallowate, isopropyl behenate, isopropyl soyate, propyl oleate, butyl oleate, butyl stearate, methyl coconate, methyl lardate, isobutyl palmitate, butyl myristate, ethyl palmitate, ethyl myristate, ethyl oleate, ethyl stearate, isobutyl stearate, isobutyl myristate and combinations thereof.

Another class of fatty esters that can be included in the composition of the present invention, either alone or in combination with the fatty esters described above, is the benzoate esters. Suitable benzoate esters include esters of benzoic acid wherein the esterifying alcohol includes about 8 carbon atoms to about 22 carbon atoms. Examples of suitable benzoate esters include, but are not limited to, the commercial products FINSOLV TN, benzoic acid esterified with fatty alcohols including about 12 to about 15 carbon atoms; FINSOLV SB, isostearyl benzoate; FINSOLV P, PPG-15 stearyl ether benzoate; or combinations thereof, all available from Finetex Inc., Elmwood Park, N.J.

Waxes, fats and oils also can be included in the oil phase of the emulsified compositions. Waxes, fats and oils increase the viscosity of the composition, impart high temperature stability to the composition, and provide emolliency. Preferred oils are triglycerides.

Specific waxes, fats and oils that can be incorporated into the oil phase of the emulsified cosmetic compositions include, but are not limited to, hydrogenated castor oil, capric/caprylic triglyceride, bayberry wax, beeswax, carnauba wax, hydrogenated jojoba oil, hydrogenated jojoba wax, hydrogenated rice bran wax, jojoba oil, lanolin wax, mink wax, ouricury wax, rice bran wax, $C_{10-18}$ triglycerides, caprylic/capric/isostearic/adipic triglyceride, caprylic/capric/lauric triglyceride, caprylic/capric/linoleic triglyceride, caprylic/capric/stearic triglyceride, castor oil, glyceryl triacetyl hydroxystearate, glyceryl triacetyl ricinoleate, glyceryl tribehenate, glyceryl trioctanoate, glyceryl triundecanoate, hydrogenated coconut oil, hydrogenated cottonseed oil, hydrogenated palm kernel oil, hydrogenated palm oil, hydrogenated tallow, hydrogenated vegetable oil, and mixtures thereof. Numerous other waxes, fats and oils are listed in the *CTFA Handbook*, at pages 27 and 49, incorporated herein by reference. Preferred waxes, fats and oils impart a waxy feel, as opposed to oily feel to the emulsified composition.

Each compound is present in the oil phase in a sufficient amount to perform its intended function. Therefore, the individual compounds in the oil phase each are present in an amount of about 0.1% to about 5%, and typically about 0.2% to about 3%, by weight of the composition.

In addition to the acid and the oil phase, the emulsified cosmetic composition also includes a sufficient amount of an emulsifier, or blend of emulsifiers, to disperse the oil phase into the continuous aqueous phase. The emulsifiers typically are fatty acid esters, fatty alcohols, ethoxylated fatty alcohols, nonionic surfactants, and mixtures thereof. The emulsifier can provide esthetic benefits to complement the oil phase, or the emulsifier can provide no benefits in addition to emulsification.

The emulsifier, or emulsifier blend, is present in the emulsified cosmetic composition in a sufficient amount to emulsify the oil phase and the aqueous phase. Typically, the emulsifier is present in an amount of about 5% to about 20%, and preferably about 8% to about 15%, by weight of the composition. The specific amount of emulsifier or blend of emulsifiers is readily determined by a person skilled in the art after considering the relative amounts of aqueous and oil phase, the identity of the ingredients in the oil phase and the aqueous phase, and the identity of the emulsifier or emulsifier blend. Numerous emulsifiers utilized by persons skilled in the art of formulating cosmetic emulsions are disclosed in the *CTFA Handbook* at pages 90–94, incorporated herein by reference.

In addition to the acid, oil phase and emulsifiers, the aqueous phase also can include other optional ingredients, such as glycerin, which is a water-soluble emollient and emulsion aid, preservatives, fragrances or dyes.

In accordance with an important feature of the present invention, the emulsified cosmetic composition also contains about 0.5% to about 2%, and preferably 0.6% to about 1.5%, by weight of a quaternized phosphate ester of structural formula I. To achieve the full advantage of the present invention, the composition contains about 0.8% to about 1.2% by weight of the quaternized phosphate ester.

Surprisingly, it was demonstrated that incorporating a quaternized phosphate ester into the emulsified cosmetic composition reduced the pH drift of the composition from about 0.2 to 0.3 pH units to about 0.15, and preferably about 0.1, pH unit or less. The quaternized phosphate ester therefore provides a composition that can be designed as a nonirritating composition, and that remains as a non-irritating composition because the pH remains essentially constant and a relatively large drop in pH is eliminated. The essentially constant pH of the emulsified composition also improves the phase stability of the composition because emulsion stability can be related to pH of the composition.

In particular, the quaternized phosphate ester of structural formula I demonstrates an ability to stabilize composition pH when the quaternized phosphate ester is incorporated into the emulsified composition in an amount of about 0.5% by weight. Above about 2% by weight of the composition, the quaternized phosphate ester provides no further benefits with respect to stabilizing pH drift, but has a tendency to impart adverse esthetic properties to the composition, such as an unacceptably low viscosity, poor color and unacceptable odor.

The quaternized phosphate esters have the general structural formula:

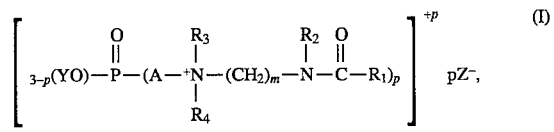

wherein $R_1$ is an aryl, an alkaryl, an alkyl, or an alkenyl group, or a hydroxyalkyl group, wherein the alkyl or hydroxyalkyl group includes about seven to about 21 carbon atoms; $R_2$ is hydrogen or an alkyl or a hydroxyalkyl group including one to about six carbon atoms; $R_3$ and $R_4$, independently, are an alkyl or a hydroxyalkyl group including one to about six carbon atoms; A is a residue of a glycol or a triol having two to about four carbon atoms, such as the residue of propylene glycol ($-OCH_2CH(OH)CH_2-$); Z is an anion, for example chloride, bromide, methosulfate, ethosulfate, and combinations thereof; m is a numeral from one to about 10; Y is selected from the group consisting of hydrogen, an alkyl group, a hydroxyalkyl group, and an aryl group, either substituted or unsubstituted, and wherein the alkyl or the hydroxyalkyl group includes one to about 22 carbon atoms; and p is a number from 1 to 3.

To achieve the full advantage of the present invention, the quaternized phosphate ester is a quaternized phosphate triester that includes the alkyl moiety of an essential fatty acid, like linoleic acid, arachidonic acid or ricinoleic acid, as the $R_1$ substituent of the compound. For example, the quaternized phosphate ester of general structural formula I that includes the alkyl moiety of an essential fatty acid as the $R_1$ substituent and wherein the number p is 3.

The quaternized phosphate esters of structural formula I are disclosed in Mayhew et al. U.S. Pat. Nos. 4,209,449 and 4,503,002, incorporated herein by reference. An example of an especially useful quaternized phosphate triester is depicted in structural formula (III), available commercially under the brandname PHOSPHOLIPID EFA, from Mona Industries, Paterson, N.J., and having the CTFA designation

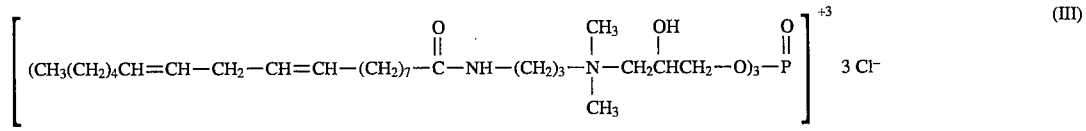

linoleamidopropyl PG-dimonium chloride phosphate. This quaternized phosphate ester has p equal to 3 and includes the alkyl moiety of linoleic acid as the substituent $R_1$. Other quaternized phosphate esters commercially available from Mona Industries include PHOSPHOLIPID PTC, PHOSPHOLIPID PTD, PHOSPHOLIPID PTS, and PHOSPHOLIPID SV, wherein the $R_1$ group is coconut, lauric, stearic and stearic, respectively.

It should be understood that the monophosphate ester (i.e., p=1) and diphosphate ester (i.e., p=2) of the quaternized phosphate ester illustrated in general structural formula I also can be used in the emulsified composition of the present invention. For example, suitable monophosphate and diphosphate esters of general structural formula I include Y as hydrogen, if the composition pH is sufficiently low such that the acid form of the phosphoric acid ester is present, as opposed to the neutralized, salt form; or Y is an alkyl group, a hydroxyalkyl group or an aryl group.

To demonstrate the new and unexpected results achieved by the present emulsified, low pH cosmetic compositions, the following compositions of Examples 1–41 were prepared. For each compositions the pH was measured over a three month period to determine pH drift. The compositions of Examples 1–41 also were observed for phase stability.

The compositions of Examples 1–41 were prepared by methods well-known in the art. In particular, the components of the aqueous phase were dissolved in the water, and the emulsifiers were blended into the oil phase. The water and oil phase then were admixed with agitation to provide an emulsified, low pH cosmetic composition. The compositions of Examples 1–41 were creams or lotions.

The compositions of Examples 1–41 are set forth below, wherein the percentages are weight percent of each ingredient present in the composition, on a 100% active basis. The compositions of Examples 1–41 also include 0.5–1% by weight magnesium aluminum silicate, 0.5–0.75% by weight aluminum starch octenylsuccinate, and a sufficient amount of ammonium hydroxide to provide an initial pH of about 3.7 to about 4.3.

| Ingredient | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Steatric Acid[1] | 1.35 | 1.5 | 1.5 | 1.5 | 1.35 | 1.35 | 1.5 | 1 | 1 |
| Glyceryl S&P-100 Stearate[2] | 5.4 | 5 | 5 | 5 | 4.5 | 5 | 5 | 5.4 | 5 |
| Stearyl Alcohol/Ceteareth-20[3] | 1.8 | 2 | 1.8 | 1.8 | 1.8 | 1.8 | 1.8 | 2 | 2 |
| Squalene[4] | 1.8 | 2 | 2 | 2 | 1.8 | 1.8 | 2 | 2 | |
| Volatile Dimethicone[5] | .45 | .75 | 1 | 1 | .75 | .75 | 1 | .4 | .75 |
| Choleth/Ceteth 24[6] | .36 | .4 | .4 | .4 | .36 | .36 | .4 | 2 | .4 |
| Cetyl Octanoate[7] | 1.8 | 2 | 2 | 2 | 1.8 | 1.8 | 2 | 2 | 2 |
| Capric/Caprylic Triglyceride[4] | 1.8 | 2 | 2 | 2 | 1.8 | 1.8 | 2 | 2 | 2 |
| Cetyl Palmitate[7] | 2 | 2 | 2 | 2 | 1.8 | 1.8 | 2 | 1 | 2 |
| Hydrogenated Castor Oil[8] | | 1 | | 1 | 1 | 1 | 1 | | 1 |
| Nonvolatile Dimethicone | .45 | .5 | | | | | | .5 | .5 |
| Cetyl/Stearyl Alcohol[10] | .45 | .5 | .5 | | | | | | .5 |
| Quaternized Phosphate Ester[11] | 1 | 1 | 1 | 1 | 1 | 1 | 1 | 1 | 1 |
| Hydroxy acid[12] | 8 | 8 | 8 | 8 | 8 | 8 | 8 | 8 | 8 |
| Glycerin | 1 | 3 | 3 | 3 | 3 | 3 | 3 | 3 | 3 |
| Aqueous Phase[13] | q.s. | q.s. | q.s. | q.s. | q.s. | q.s. | q.s. | q.s. | q.s. |
| % Oil Phase[14] | 17.66 | 19.65 | 18.2 | 18.7 | 16.96 | 17.46 | 18.7 | 18.8 | 17.15 |
| pH initial | | | | | 3.97 | 3.94 | 3.93 | 3.87 | 3.86 |
| 1 week | 3.85 | 3.86 | 3.86 | 3.84 | 3.88 | 3.87 | 3.89 | 3.81 | 3.81 |
| 1 month | 3.79 | | 3.93 | 3.93 | 3.93 | 3.91 | 3.85 | 3.87 | 3.86 |
| 2 month | 3.83 | 3.79 | 3.87 | 3.81 | 3.84 | 3.83 | 3.83 | 3.84 | 3.79 |
| 3 month | 3.77 | 3.81 | 3.77 | 3.80 | 3.80 | 3.79 | 3.80 | 3.83 | 3.83 |
| Phase Stability[15] | s.s.[16] after 1 mo. | n.s., g.v. | n.s., g.v. | n.s., g.v. | n.s., g.v. | n.s., g.v. | n.s., g.v. | n.s., g.v. | n.s., g.v. |

| Ingredient | Ex. 10 | Ex. 11 | Ex. 12 | Ex. 13 | Ex. 14 | Ex. 15 | Ex. 16 | Ex. 17 |
|---|---|---|---|---|---|---|---|---|
| Steatric Acid[1] | 1 | 1 | .95 | | .5 | 1.35 | 1.35 | 1 |
| Glyceryl S&P-100 Stearate[2] | 5 | 5.4 | 5.13 | 5.4 | 5.4 | 5.4 | 5.4 | 5.4 |
| Stearyl Alcohol/Ceteareth-20[3] | 1.8 | 1.8 | 1.8 | 1.8 | 1.8 | 1.8 | 1.8 | 1.8 |
| Squalene[4] | 2 | 2 | 1.9 | 1.8 | 1.8 | 1.8 | 1.8 | 1.8 |
| Volatile Dimethicone[5] | 1 | 1 | .95 | .75 | .75 | .45 | .45 | .45 |
| Choleth/Ceteth 24[6] | .4 | .4 | .38 | .36 | .36 | .36 | .36 | .36 |
| Cetyl Octanoate[7] | 2.6 | 2.6 | 2.47 | 1.8 | 1.8 | 2.2 | 1.8 | 1.8 |
| Capric/Caprylic Triglyceride[4] | 2 | 2 | 1.9 | 1.8 | 1.8 | 1.8 | 1.8 | 1.8 |
| Cetyl Palmitate[7] | 2 | 2 | 1.9 | 1.8 | 1.8 | 1.8 | 1.8 | 1.8 |
| Hydrogenated Castor Oil[8] | 1 | 1 | .95 | 1 | 1 | 1 | 1 | 1 |
| Nonvolatile Dimethicone | | | | | | .45 | .45 | .45 |
| Cetyl/Stearyl Alcohol[10] | | | | | | | | |
| Quaternized Phosphate Ester[11] | 1 | 1 | 1 | 1 | 1 | 1 | 1 | 1 |
| Hydroxy acid[12] | 8 | 8 | 8 | 8 | 8 | 8 | 8 | 8 |
| Glycerin | 3 | 3 | 3 | 3 | 3 | 2 | 2 | 3 |
| Aqueous Phase[13] | q.s. | q.s. | q.s. | q.s. | q.s. | q.s. | q.s. | q.s. |
| % Oil Phase[14] | 18.8 | 19.2 | 18.33 | 16.51 | 17.01 | 18.41 | 18.01 | 17.66 |
| pH initial | 3.90 | | | 3.90 | 3.90 | 3.91 | 3.90 | 3.90 |
| 1 week | 3.86 | 3.86 | 3.89 | 3.86 | 3.87 | 3.89 | 3.86 | 3.93[17]/3.87 |
| 1 month | 3.87 | 3.89 | 3.92 | 3.92 | 3.92 | 3.90 | 3.88 | 3.85[17]/3.92 |
| 2 month | 3.87 | 3.84 | 3.82 | 3.85 | 3.83 | 3.86 | 3.85 | —[17]/3.85 |
| 3 month | 3.85 | 3.87 | 3.83 | 3.86 | 3.85 | 3.85 | 3.85 | 3.80[17]/3.85 |
| Phase Stability[15] | n.s., g.v. | n.s., g.v. | n.s., g.v. | n.s., g.v. | n.s., g.v. | n.s., g.v. | n.s., g.v. | n.s., g.v. |

| Ingredient | Ex. 18 | Ex. 19 | Ex. 20 | Ex. 21 | Ex. 22 | Ex. 23 | Ex. 24 | Ex. 25 |
|---|---|---|---|---|---|---|---|---|
| Steatric Acid[1] | .5 | 1 | 1 | 1.35 | 1.35 | 1.35 | 1.35 | 1.35 |
| Glyceryl S&P-100 Stearate[2] | 5.4 | 6 | 6 | 5 | 5 | 5 | 5 | 5 |

-continued

| Ingredient | | | | | | | | |
|---|---|---|---|---|---|---|---|---|
| Stearyl Alcohol/Ceteareth-20[3] | 1.8 | 2 | 2 | 1.5 | 1.5 | 1.5 | 1.8 | 1.8 |
| Squalene[4] | 1.8 | 2 | 2 | 1.8 | 1.8 | 1.8 | 1.8 | 1.8 |
| Volatile Dimethicone[5] | .75 | .75 | 1 | .45 | .45 | .45 | .45 | .45 |
| Choleth/Ceteth 24[6] | .36 | .4 | .4 | .36 | .36 | .36 | .36 | .36 |
| Cetyl Octanoate[7] | 2.3 | 2 | 2.6 | 2.2 | 2.2 | 1.8 | 1.8 | 1.8 |
| Capric/Caprylic Triglyceride[4] | 1.8 | 2 | 2 | 1.8 | 1.8 | 2.2 | 1.8 | 1.8 |
| Cetyl Palmitate[7] | 1.8 | 2 | 2 | | | | | |
| Hydrogenated Castor Oil[8] | 1 | 1 | 1 | 1 | | | | |
| Nonvolatile Dimethicone | | .5 | | .45 | .45 | .45 | .45 | .45 |
| Cetyl/Stearyl Alcohol[10] | | .5 | | | | | | |
| Quaternized Phosphate Ester[11] | 1 | 1 | 1 | 1 | 1 | 1 | 1 | 1 |
| Hydroxy acid[12] | 8 | 8 | 8 | 8 | 8 | 8 | 8 | 8 |
| Glycerin | 3 | 3 | 3 | 3 | 2 | 2 | 2 | 2 |
| Aqueous Phase[13] | q.s. | q.s. | q.s. | q.s. | q.s. | q.s. | q.s. | q.s. |
| % Oil Phase[14] | 17.51 | 20.15 | 20 | 16.71 | 16.71 | 16.71 | 16.61 | 16.61 |
| pH initial | 3.84 | 3.90 | 3.92 | 3.95 | 3.76 | 3.75 | 3.85 | 3.84 |
| 1 week | 3.87 | 3.93 | 3.91 | 3.84 | 3.68 | 3.64 | 3.75 | 3.70 |
| 1 month | 3.92 | 3.92 | 3.85 | | | | | |
| 2 month | 3.84 | 3.86 | | | | | | |
| 3 month | 3.80 | 3.83 | 3.83 | | | | | |
| Phase Stability[15] | n.s., g.v. | n.s., g.v. | n.s., g.v. | low viscosity | low viscosity | low viscosity | low viscosity | low viscosity |

| Ingredient | Ex. 26 | Ex. 27 | Ex. 28 | Ex. 29 | Ex. 30 | Ex. 31 | Ex. 32 | Ex. 33 |
|---|---|---|---|---|---|---|---|---|
| Steatric Acid[1] | 1.2 | 1.5 | 1.5 | 1.35 | 1.35 | 1 | | 1.5 |
| Glyceryl S&P-100 Stearate[2] | 4.8 | 6 | 6 | 5.4 | 5.4 | 6 | 6 | 6 |
| Stearyl Alcohol/Ceteareth-20[3] | 1.6 | 2 | 2 | 1.8 | 1.8 | 2 | 2 | 2 |
| Squalene[4] | 1.6 | 2 | 2 | 1.5 | 1.8 | 2 | 2 | 2 |
| Volatile Dimethicone[5] | .4 | .5 | .5 | .45 | .45 | | .5 | .5 |
| Choleth/Ceteth 24[6] | .32 | .4 | .4 | .36 | .36 | 4 | .4 | .4 |
| Cetyl Octanoate[7] | 1.6 | 2 | 2 | 1.8 | 1.8 | 2 | 2 | 2 |
| Capric/Caprylic Triglyceride[4] | 1.6 | 2.5 | 2 | 1 | 1 | 1 | 2 | 2 |
| Cetyl Palmitate[7] | 1.6 | 2 | 2 | 2 | 2 | 2 | 2 | 2 |
| Hydrogenated Castor Oil[8] | | | | | | | 1 | |
| Nonvolatile Dimethicone | .4 | .5 | .5 | .45 | .45 | .25 | .5 | .5 |
| Cetyl/Stearyl Alcohol[10] | .4 | .5 | .5 | .45 | .45 | .5 | .5 | .5 |
| Quaternized Phosphate Ester[11] | 1 | 1 | 1 | 1 | 1 | .6 | | |
| Hydroxy acid[12] | 8 | 8 | 8 | 8 | 8 | 8 | 8 | 8 |
| Glycerin | 2 | 2 | 2 | 1 | 1 | 1 | 1 | 1 |
| Aqueous Phase[13] | q.s. | q.s. | q.s. | q.s. | q.s. | q.s. | q.s. | q.s. |
| % Oil Phase[14] | 15.52 | 19.9 | 19.4 | 16.56 | 16.86 | 17.15 | 19.9 | 19.4 |
| pH initial | 3.87 | 3.89 | 3.91 | 3.90 | 3.85 | 3.75 | 3.74 | 3.78 |
| 1 week | 3.81 | 3.79 | 3.80 | 3.89 | 3.86 | 3.67 | 3.56 | 3.56 |
| 1 month | | | 3.83 | 3.81 | 3.83 | 3.71 | 3.57 | 3.58 |
| 2 month | | | 3.92 | 3.86 | 3.86 | 3.75 | 3.50 | 3.55 |
| 3 month | | | 3.84 | 3.80 | 3.84 | 3.71 | 3.52 | 3.55 |
| Phase Stability[15] | marginal viscosity | sufficient viscosity | n.s., marginal viscosity | n.s. | n.s. | n.s. | sep. | sep. |

| Ingredient | Ex. 34 | Ex. 35 | Ex. 36 | Ex. 37 | Ex. 38 | Ex. 39[19] | Ex. 40[19] | Ex. 41[20] |
|---|---|---|---|---|---|---|---|---|
| Steatric Acid[1] | 2 | | 1.5 | 2 | | | | |
| Glyceryl S&P-100 Stearate[2] | 6 | 6 | 6 | 6 | 4 | 5 | 3.3 | |
| Stearyl Alcohol/Ceteareth-20[3] | 2 | 2 | 2 | 2 | 2 | 3 | 2.2 | |
| Squalene[4] | 2 | 2 | 2 | 2 | 3 | | | |
| Volatile Dimethicone[5] | .5 | .5 | .5 | | | | | .43 |
| Choleth/Ceteth 24[6] | .4 | .4 | .4 | .4 | .4 | .4 | | |
| Cetyl Octanoate[7] | 2 | 2 | 2 | 2 | 2 | 2 | 2 | |
| Capric/Caprylic Triglyceride[4] | 2 | 2 | 2 | 2 | 2 | 2 | | |
| Cetyl Palmitate[7] | 2 | 2 | 2 | 2 | | | | .66 |
| Hydrogenated Castor Oil[8] | | 1 | | | | | | 1.31 |
| Nonvolatile Dimethicone | .5 | .5 | .5 | .5 | .1 | .3 | | |
| Cetyl/Stearyl Alcohol[10] | .5 | .5 | .5 | .5 | .5 | 1 | 1.1 | .75 |
| Quaternized Phosphate Ester[11] | | 1 | 1 | 1 | 1 | | .7 | .7 |
| Hydroxy acid[12] | 8 | 8 | 8 | 8 | 8 | 3.5 | 3.5 | 3.5 |
| Glycerin | 1 | 1 | 1 | 1 | 5 | 10 | 10 | 10 |
| Aqueous Phase[13] | q.s. | q.s. | q.s. | q.s. | q.s. | q.s. | q.s. | q.s. |
| % Oil Phase[14] | 19.9 | 18.9 | 19.4 | 19.4 | 16.15 | 18.2 | 11.9 | 20.49 |
| pH initial | | | 3.86 | | | 4.48 | 4.10 | 4.14 |
| 1 week | 3.80 | 3.87 | 3.80 | 3.96 | 3.80 | | 4.10 | 4.13 |
| 1 month | 3.80 | 3.82 | 3.80 | 3.72 | 3.87 | 4.28 | 4.23 | 4.25 |
| 2 month | 3.77 | 3.79 | 3.79 | | 3.87 | | 4.09 | 4.13 |
| 3 month | 3.82 | | 3.73 | 3.83 | 3.83 | | 4.17 | 4.17 |
| Phase Stability[15] | sep., g.v. | n.s. | n.s. | n.s. | sep. | n.s. | n.s. | n.s. |

[1]emulsifier;
[2]ARLACEL 165, available from ICI Americas, Wilmington, DE, a primary emulsifier;
[3]PROMULGEN G, available from Amerchol Corp., Edison, NJ, a secondary emulsifier;

[4)] an emollient;
[5)] Dow Corning DC 200 Fluid, available from Dow Corning Corp., Midland, MI;
[6)] a tertiary emulsifier;
[7)] an emollient and emulsion whitener;
[8)] phase stabilizer and esthetic aid;
[9)] Dow Corning Fluid 350, available from Dow Corning, Midland, MI;
[10)] bodifier, whitener and viscosity builder;
[11)] PHOSPHOLIPID EFA, available from Mona Industries, Paterson, NJ;
[12)] glycolic acid;
[13)] includes water, optional polymers, thickeners and neutralizing agents;
[14)] total oil phase in the composition;
[15)] storage stability at 120° F.;
[16)] abbreviations: s.s.-slight separation; n.s.-separation; and g.v.-good viscosity;
[17)] embodiment with fragrance/embodiment without fragrance;
[18)] cyclomethicone;
[19)] composition also included 2% hydrogenated polybutene, 2% tridecyl behenate, 0.5% pentaerythritol tetraoctanoate and 0.05–0.5% hydroxyethylcellulose (Ex. 29) or xanthan gum (Ex. 40); and
[20)] composition also includes 4.56% of an ester blend (a blend of tridecyl stearate, neopentyl glycol dicaprate/dicaprylate, and tridecyl trimellitate), 2.63% PEG-20 methyl glucose sesquistearate, 5.26% methyl glucose sesquistearate, 2.63% PPG-2 myristyl ether propionate, and 0.05–0.5% xanthan gum.

The compositions of Examples 1–41 illustrate that emulsified, low pH cosmetic compositions containing about 0.5% to about 2% by weight of a quaternized phosphate ester of structural formula I exhibit an essentially constant pH. Compositions of Examples 1–41 that incorporated the quaternized phosphate ester exhibited a pH drift of 0.15 pH unit or less, and usually 0.10 pH unit or less. In contrast, compositions excluding the quaternized phosphate ester (Examples 32, 33 and 39) exhibited a pH drift of greater than 0.2 pH units.

The compositions of Examples 1–41 also illustrate that when the oil phase is less than about 17% by weight of the composition, the oil phase has a greater tendency to separate from the aqueous phase (Example 1), but that an oil, like hydrogenated castor oil, helps maintain phase stability (Example 2). However, an oil is not necessary to achieve phase stability, as illustrated in Examples 3, 8, 29–31, 36 and 37, which are phase stable compositions in the absence of an oil. The oil also helps to provide a viscosity that is sufficiently high for consumer acceptance.

The compositions of Examples 42 and 43 illustrate that the acid in the emulsified cosmetic composition can be a β-hydroxy acid (Example 42) or a combination of an α-hydroxy acid and a β-hydroxy acid (Example 43).

| Ingredient | Ex. 42 | Ex. 43 |
|---|---|---|
| Steatric Acid[1)] | .5 | .5 |
| Glyceryl S&P-100 Stearate[2)] | 5.4 | 5.4 |
| Stearyl Alcohol/Ceteareth-20[3)] | 1.8 | 1.8 |
| Squalene[4)] | 1.8 | 1.8 |
| Volatile Dimethicone[5)] | .75 | .75 |
| Choleth/Ceteth 24[6)] | .86 | .36 |
| Cetyl Octanoate[7)] | 2.3 | 2.3 |
| Capric/Caprylic Triglyceride[4)] | 1.8 | 1.8 |
| Cetyl Palmitate[7)] | 1.8 | 1.8 |
| Hydrogenated Castor Oil[8)] | 1 | 1 |
| Nonvolatile Dimethicone | | |
| Cetyl/Stearyl Alcohol[10)] | | |
| Quaternized Phosphate Ester[11)] | 1 | 1 |
| Salicylic Acid[21)] | 1 | 1 |
| Glycolic Acid[22)] | | 8 |
| Glycerin | 3 | 3 |
| Aqueous Phase[13)] | q.s. | q.s. |
| % Oil Phase[14)] | 17.51 | 17.51 |
| pH initial | 2.87 | 3.74 |
| 1 week | | |
| 1 month | | |
| 2 month | 2.73 | 3.68 |
| 3 month | | |
| Phase Stability[15)] | | |

[21)] a β-hydroxy acid; and
[22)] an α-hydroxy acid.

Obviously, many modifications and variations of the invention as hereinbefore set forth can be made without departing from the spirit and scope thereof and therefore only such limitations should be imposed as are indicated by the appended claims.

I claim:

1. An emulsified cosmetic composition comprising:
   (a) about 2% to about 20% by weight of an organic acid selected from the group consisting of glycolic acid and salicylic acid;
   (b) about 10% to about 50% by weight of an oil phase;
   (c) about 5% to about 20% by weight of an emulsifier or emulsifier blend;
   (d) about 0.5% to about 2% by weight of linoleamidopropyl PG-dimonium chloride phosphate; and
   (e) water,
   wherein the composition has a pH of about 3.7 to about 4.5 and a pH drift of about 0.15 pH unit or less.

2. The composition of claim 1 having a pH drift of about 0.1 pH unit or less.

3. The composition of claim 1 comprising about 3% to about 15% by weight of the organic acid.

4. The composition of claim 1 comprising about 15% to about 40% by weight of the oil phase.

5. The composition of claim 1 comprising about 10% to about 20% by weight of the oil phase, and further comprising about 0.05% to about 0.5% of an organic polymer, an organic thickener or an inorganic thickener.

6. The composition of claim 5 wherein the polymer or thickener is selected from the group consisting of magnesium aluminum silicate, aluminum starch octenylsuccinate, a polyvinylalcohol, a polybutene, a polyethylene glycol, a polyethylenimine, xanthan gum, carrageenen, hydroxyethylcellulose, hydroxypropylcellulose, hydroxypropyl guar, methylcellulose, tragacanth gums karaya gum, and mixtures thereof.

7. The composition of claim 1 wherein the oil phase comprises a silicone, a hydrocarbon, an oil, a fat, a wax, a water-insoluble fatty alcohol or fatty acid having 8 to 22 carbon atoms, a water-insoluble fatty ester having 9 to 34 carbon atoms, and mixtures thereof.

8. The composition of claim 1 comprising about 0.6% to about 1.5% by weight of the linoleamidopropyl PG-dimonium chloride phosphate.

9. The composition of claim 1 comprising about 0.8% to about 1.2% by weight of the linoleamidopropyl PG-dimonium chloride phosphate.

10. A method of improving the stability of an emulsified cosmetic composition comprising
    (a) about 2% to about 20% by weight of an organic acid selected from the group consisting of glycolic acid and salicylic acid;

(b) about 10% to about 50% by weight of an oil phase;
(c) about 5% to about 20% by weight of an emulsifier or emulsifier blend;
(d) water, and having a pH of about 3.7 to about 4.5, said method comprising the step of incorporating about 0.5% to about 2% by weight of linoleamidopropyl PG-dimonium chloride phosphate into the composition such that the composition has a pH drift of about 0.15 pH unit or less.

11. The method of claim 10 wherein a sufficient amount of the quaternized phosphate ester is incorporated into the composition such that the pH drift is about 0.1 pH unit or less.

* * * * *